United States Patent
Cerny

(10) Patent No.: US 6,699,474 B1
(45) Date of Patent: *Mar. 2, 2004

(54) VACCINE AND IMMUNSERUM AGAINST DRUGS OF ABUSE

(76) Inventor: Erich Hugo Cerny, I rue Piachaud, Geneva I204 (CH)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 137 days.

(21) Appl. No.: 08/933,268

(22) Filed: Sep. 18, 1997

Related U.S. Application Data

(63) Continuation of application No. 08/418,850, filed on Apr. 4, 1997, now abandoned, which is a continuation of application No. 07/846,999, filed as application No. PCT/CH91/00016 on Jan. 17, 1991, now abandoned.

(30) Foreign Application Priority Data

Aug. 20, 1990 (CH) .............................................. 2720-90

(51) Int. Cl.$^7$ ............................................. A61K 39/395
(52) U.S. Cl. ............................... 424/175.1; 424/193.1; 530/389.8; 530/388.9; 514/810; 514/812
(58) Field of Search .......................... 530/389.8, 388.9, 530/403; 514/810, 812, 813; 424/175.1, 193.1

(56) References Cited

U.S. PATENT DOCUMENTS

| | | | |
|---|---|---|---|
| 3,642,981 A | * 2/1972 | Cuculis et al. ................. | 424/88 |
| 3,709,868 A | * 1/1973 | Spector ....................... | 260/121 |
| 3,766,162 A | * 10/1973 | Spector ....................... | 530/389.8 |
| 3,867,366 A | * 2/1975 | Rubenstein et al. ........... | 424/88 |
| 4,045,420 A | 8/1977 | Soffer et al. .................. | 424/88 |
| 4,375,414 A | 3/1983 | Strahilevitz ................. | 210/638 |
| 4,620,977 A | * 11/1986 | Strahilevitz ................. | 424/88 |

FOREIGN PATENT DOCUMENTS

| | | |
|---|---|---|
| DE | 2202441 | 3/1973 |
| DE | 25 48 196 | 4/1977 |
| EP | 0 311 383 | 4/1989 |
| EP | 0 363 041 | 4/1990 |
| RU | 792869 | 3/1982 |
| RU | 1123704 | 11/1984 |

OTHER PUBLICATIONS

Pentel et al., "In Rats Using a Drug–Specific Monoclonal Redistribution of Tricyclic Antidepressants Antibody: Dose–Response Relationship," Drug Metabolism & Disposition 19:24–28 (1991).*
Colburn, W.A., "Specific Antibodies and Fab Fragments to Alter The Pharmacokinetics and Reverse the Pharmacologic/Toxicologic Effects of Drugs", Drug Metabolism Reviews 11: 223–262 (1980).*
McConnell, I., The Immune System (Blackwell Scientific Publications, Boston MA) pp 157–159 (1981).
Bonese, et al., Nature, 252:708–710, Dec. 1994.*
Bagasra, "Reply to Dr. Gallacher", in Galacher, Immunopharmacology, 27:79–84, Feb. 1994.*
Stedman's Medical Dictionary, 24th ed., Williams & Wilkens, Baltimore, 1982.*
Pentel et al., Pharmacology Biochemistry and Behavior, vol. 65, No. 1, 191–198, 2000.*
Hieda et al., The Journal of Pharmacology and Experimental Therapetics, 283(2):1076–1081, 1997.*
Hieda et al., Psychopharmacology 143:150–157, 1999.*
Self D.W., Nature, 378:726–727, Jan. 1995.*
Carrera et al., Nature, 378:727–730, Dec. 1995.*
P. H. Chuong, C. Labarre, J. Bory and G. Le Moan, "Study of Antibodies Anti–Aspirine, Which Were Elicited in a Rabbit," Annales Pharmaceutiques Francaises, vol. 35, No. 7/8 (1977).
K. F. Bonese et al., "Changes in Heroin Self–Administration by a Rhesus Money After Morphine Immunisation," Nature, vol. 252, Dec. 20/27, pp. 708–10 (1974).
A. Killian, K. Bonese, R. M. Rothberg, B. H. Wainer and C. R. Schuster, "Effects of Passive Immunization Against Morphine on Heroin Self–Administration," Pharmacology Biochemistry & Behavior, vol. 9, pp. 347–352 (1978).
Weir, D.M., Weir's handbook of experimental immunology: in four volumes 4th ed. 1986, Cambridge, Mass., USA: Blackwell Science. 4v.
Bonese, K.F. et al., Changes in heroin self–administration by a rhesus monkey after morphine immunisation. Nature, 1974. 242 (5485): p. 708–10.
Cerny, E.H. et al., Preclinical development of "a vaccine against smoking." Onkologie, 2002. 25(5): p. 406–11.
Langone, J.J. et al., Nicotine and its meatabolites. Radio–immunoassays for nicotine and continine. Biochemistry, 1973. 12(24): p. 5025–30.
Carrera, M.R. et al., A second–generation vaccine protect against the psychoative effects of cocaine. Proc Natl Acad Sci USA, 2001. 98(4): p. 1988–92.
Hieda, Y. et al., Vaccination against nicotine during continued nicotine administration in rats . . . , Int. J. Immunopharmacol, 2000. 22(10): p. 809–19.

(List continued on next page.)

Primary Examiner—Sheela Huff
(74) Attorney, Agent, or Firm—Clifford W. Browning; Woodard, Emhardt, Moriarty, McNett & Henry LLP

(57) ABSTRACT

Addictive drugs like cocaine, heroin or amphetamines are spreading in an epidemic manner in the western world and are an important factor in the spread of the acquired immune deficiency syndrome AIDS (multiple use of infected needles among drug addicts) the present invention describes a vaccine and immunoserum against drugs. The vaccine contains the drug bound to a carrier protein in order to produce antibodies against the drugs in the affected person. The use of the drug in the presence of the antibodies deactivates the drug. The desired drug effect is thus eliminated and the vicious circle between stimulation and application is broken.

20 Claims, No Drawings

OTHER PUBLICATIONS

Carrera, M.R. et al., Suppression of psychoactive effects of cocaine by active immunication. Nature, 1995. 378(6558): p. 727–30.

Self, D.W., Drug Addiction. Cocaine abuse takes a shot. Nature, 1995. 378(6558): p. 666–7.

Lloyd, B.L. et al., Contrasting rates of reversal of digoxin toxicity by digoxin–specific IgG and Fab fragments. Circulation, 1978. 58(2): p. 280–3.

Arend, W.P. et al., Serum disappearance and catabolism of homologous immunoglobulin fragments in rats. Clin Ecp Immunol, 1975. 22(3): p. 502–13.

Greenblatt, D.J. et al., Drug therapy. Clinical Pharmacokinetics (first of two parts). N Engl J Med, 1975. 293(14): p. 702–5.

Greenblatt, D.J. et al., Clinical pharmacokinetics (second of two parts). N Eng J Med, 1975. 293(19): p. 964–70.

\* cited by examiner

VACCINE AND IMMUNSERUM AGAINST DRUGS OF ABUSE

This application is a continuation of application Ser. No. 08/418,850, filed Apr. 7, 1997, now abandoned filed Apr. 2, 1992, now abandoned, which is a 391 of PCT/CH97/00016 filed Jan. 17, 1991, which is a continuation of Ser. No. 07/846,999, The invention describes a procedure for the manufacturing of a vaccine against drugs that can generate a dependence, wherein one or more drugs are linked as a hapten to a carrier substance in order to get the hapten antigenic, or wherein one or more drugs are chemically cross linked as a hapten in order to get an antigenic effect without a carrier compounds. The invention describes also a procedure wherein the vaccines, manufactured according to a process wherein one or more drugs are linked as a hapten to a carrier substance in order to get the hapten antigenic, are used as antigens for the production of antibodies against drugs, which may cause a dependence.

Dependence on drugs is often understood as a physical and psychical dependence. One or the other component can be dominant, but both components are normally present in an addict. Drugs which cause a psychical dependence are e.g. opiates, barbiturates, alcohol, cigarettes, anxyolytic drugs and some sedatives. Psychological dependence on the other hand is described as a desire for a drug, which temporarily becomes extinct, after ingestion of the drug and when the desired effect has taken over. Examples for a drug which can generate a psychical dependence are opiates and cigarettes.

A successful therapy implies a liberation of the psychical as well as the physical component of dependence. The classical therapy tries to obtain a disintoxication through a successive diminution or in some cases (methadone) substitution of the drug. The psychical component of dependance is treated through a program of rehabilitation.

The vaccine of this invention allows a new approach to the therapy and prevention patients, which are addicted to a drug. The continued use of the drug in the presence of the antibody after vaccination inactivates the drug and stimulates the production of new specific antibodies. The desired drug effect is therefore eliminated and the vicious circle between stimulation and application is interrupted.

The new vaccine broadens the application of vaccines into the field of drugs. There are the following fundamental differences between a classical vaccine ant the present vaccine: 1) The vaccine is not directed against an infectious agent but against a drug. 2) The typical application of this vaccine is not preventive but therapeutic. 3) The antigen against which the vaccine is directed is in most cases not by itself antigenic, but must be bound to a carrier protein in order to elicit antibodies. 4) The effect of the drug which causes dependence is based on the interaction of the drug with the receptor. This interaction is eliminated through binding of the antibody with the drug.

It is therefore a goal of this invention to describe a vaccine against drugs of abuse:

1) Which is directed against one or more drugs which cause dependence and which is linked to a carrier protein in order to make the drug immunogenic.
2) Which is effective against drugs causing a physical dependance as well as against drugs causing a psychical dependence.
3) Which can be applied therapeutically (a drug addict is vaccinated in order to inactivate the drug) as well as preventively (in order to protect the fetus of a drug addict pregnant woman from the direct damage of the drug as well as a later dependence on the drug).
4) Which can be directed against all kind of drugs: for example opiates and opiate-like drugs, marihuana, cocaine, amphetamine, antipsychotic drugs, barbiturates and other sedatives, psychomimetic drugs, anticholinergic drugs as well as compounds which contaminate these drugs.
5) Which typically activates the B-cell branch of the immune system, but which may gain an additional efficiency through the activation of the T-cell arm of the immune system or through an allergenic effect.

Definitions

Drugs, which may cause a dependance: All compounds, which in the largest sense of the term may cause a physical or psychical dependence after one or repeated application. A drug elicits a physical dependence, if a withdrawal of the drug causes withdrawal symptoms. Psychical dependance on the other hand is caused by a drug to which the addict has gotten used and which causes with the addict a desire for a specific effect. Drugs which may cause a dependance are among others: cocaine and cocaine derivatives (cocaine consumed by drugs addicts contains frequently among other compounds in addition mannitol, lactose, nicotine, effedrine, caffeine, procaine and amphetamines), barbiturates and other sedatives, benzodiazepine, methaqualone, glutethimide, chloral hydrate, methyprylon, paraldehyde and bromides, antipsychotic drugs, psychomimetic drugs like phenylcyclidine or LSD (lysergic acid diethylamide), phenylcyclidin and analog compounds, amphetamine and tryptamine derivatives, psylocybine, volatile nitrite and anticholinergic drugs.

Components of drugs: drugs are not used all the time in a chemically pure form and are often mixed with other compounds. It may under certain conditions be an advantage to direct the vaccine against more than one compound in order to obtain a better protective effect.

Vaccine: a preparation which contains an immunogen being able to activate the B-cell arm and eventually also the T-cell arm of the immune system. The immunogen of the vaccine of this invention is typically a drug, which is bound as a hapten to the carrier substance. The binding between hapten and carrier can be covalent or ionic or be based on van der Waal forces or hydrogen bridges. The linkage may also contain one or more atoms forming a bridge. A drug can also be rendered immunogenic through a simple chemical crosslinking (for example through glutaraldehyde) in order to gain a molecular weight in excess of 5000 Dalton. It is in these cases not necessary to use a carrier compound.

The manufacturing process of the vaccine contains typically two steps: 1) Conjugation: the drug is linked to the carrier compound 2) Purification: the hapten-carrier conjugate is purified from products of the conjugation procedure and dissolved into a physiological solution. The conjugation can be performed in an organic solvent or in a aqueous environment. Substances, which are frequently used for coupling are: carbodiimides, imidoesters, N-hydroxysuccinimid ester or there water-soluble sulfo-derivatives, maleimid-derivatives and phenyl azides.

The purification is usually done by dialysis or with the help of gel- or ion chromatography. The hapten-carrier conjugate has mostly a molecular weight exceeding 100 000 Dalton and can therefore easily be purified from an excess of coupling substance, which typically has a molecular weight under 500 Dalton. Preferred methods of separation are extensive dialysis with dialysis tubing in an aqueous solution, for example through multiple exchange of Phosphate Buffered Saline (PBS) or chromatography using a Sephadex G 25 column (Pharmacia LKB Biotechnology, Bromma, Sweden). Steril-filtration with a filter having a pore size of 0.2 micrometer and the removal of pyrogenic material are the final steps of the purification.

Vaccine for preventive purposes: the person to be vaccinated is not yet drug dependant. A candidate suitable for a preventive vaccination may for example be a baby, which obtains the drug trough the mothers milk.

Vaccine for therapeutic purposes: The person to be vaccinated is already drug addicted or has started to use the drug. A person suitable for the vaccine is for example a morphine addict, which intends to get disintoxicated.

Immunization against drugs: With patients which suffer from symptoms of intoxication through drugs, there is no time to illicit with the help of a vaccine antibodies against the drug. It is possible to help in such cases through direct application of specific antibodies of human or animal origin. The specific antibody links in a short period of time after application to the drug and the immune complexes are eliminated through the reticulo-endothelial system. This leads to a removal of toxic compounds from the body. It is possible to use a mixture of antibodies against different drugs, because in lots of cases it is not clear with which drug the patient got intoxicated. The antibodies used may be monoclonal or polyclonal antibodies. Monoclonal antibodies are generated in vitro through fusion with a B-cell line containing the genetic material for the specific immunoglobulin. The hybride cell line so generated secretes only antibodies of the desired specificity. There is also the possibility to obtain monoclonal antibodies through transformation of a B cell with the help of a Epstein-Barr virus infection.

It is possible to give the antibodies orally, because patients showing symptoms of an overdose have often not yet absorbed entirely the drug. The antibodies have to be applied in this case in a capsule protecting them from digestion in the stomach and small gut.

Antibodies: This is a class of plasma proteins, which are produced by the B-cells of the immune system after stimulation through an antigen. Human antibodies are immunoglobulins of the Ig G, M, A, E or D class.

Antigen: This is a compound with the ability to elicit an response of the immune system. Antigens are typically proteins, but they can also contain sugars or lipid moieties. Antigens typically have a molecular weight of over 10 000 Dalton.

Haptens: These are small molecules, which are not able to elicit an immune answer only by themselves. A hapten has to be linked to a carrier in order to become antigenic. The immune answer to a hapten-carrier can be directed against the hapten, the carrier or both compounds. The hapten of the present invention is normally a drug, a metaboliponent of a drug as for example a component of cigarette smoke.

Some drugs are rapidly metabolized after absorption by the body. Morphine for example is rapidly transformed into morphine-3-glucuronate and morphine-6-glucuronate. It may therefore in certain cases be an advantage, if metabolites are used as a hapten in place of the original drug.

Carrier substance: The problem of eliciting antibodies against a small molecule (hapten) is resolved by linking the small molecule to a carrier. This linkage makes the hapten immunogenic, this means antibodies are generated after injection into the body. The binding of the hapten to the carrier protein is often covalent, but it can be ionic or be effected through a chemical component bridging the hapten and the carrier. The carrier is typically a protein, but it can also contain sugar and fat in mono- or polymer form. Under certain conditions it is possible to crosslink the hapten and no carrier substance is needed in order to make it immunogenic.

Antigen/antibody interaction: The interaction of a specific antibody with the surface of the corresponding antigen (hapten plus carrier compound) is reversible and the complex can dissociate depending on the force of binding. There is an interaction due to the fact that the two partners have on their surface a complementary shape of their electron clouds (similar as a key with the look). This interaction is based on hydrogen bridges, the van der Waals force, electrostatic force and hydrophobic interaction.

Adjuvant: This is a compound or mixture of compounds which are added to the vaccine in order to enhance the efficiency of the antibody production or to help generate a specific class of antibodies as for example IgM immunoglobulins or antibodies able to bind complement. Substances, which can be used as adjuvant are for example mineral oils, derivatives of aluminium or compounds of mycobacteria. The vaccines of this invention can be used with or without adjuvant.

Different ways to apply the vaccine: The vaccine can be injected intravenously, intramuscularly, subcutaneously or intradermaly. It can also be given orally (e.g. in a capsule, protected against digestion in the stomach and small bowel). It is in certain cases also possible to give the vaccine as an aerosol or onto the skin for an absorption through the skin. The vaccine can be given one time or more than one time.

In order to improve the understanding of the invention the following examples are given.

EXAMPLE 1

This example shows with the help of a mouse model how antibodies are generated and how the drug is eliminated from the circulation after vaccination against morphine derivatives or barbiturates.

Conjugation of the hapten to the carrier:

The method of Wainer is used in order to synthesize morphine-6-hemisuccinate (Wainer B. B. et al., 1972, Science 176,1143–45, Wainer B. B. et al., 1972, Science 178,647–8) and to bind it to Bovine Serum Albumin (BSA). An other preparation is made by transforming morphine into 3-0-carboxy-methylmorphine by reaction of the free base of sodium-beta-chlorazetate in absolute alcohol. Carboxymethyl-morphine (8 mg) is dissolved in 2 ml of distiled water containing 10 mg BSA and 8 mg of 1-ethyl-3-(3-dimethylaminopropyl)carbodiimide are added after adjusting the pH of the solution to 6. After incubation at room temperature, the mixture is extensively dialysed against Phosphate Buffered Saline (PBS).

The following method is used in order to obtain a barbiturate-Keyhole Lympet Hemocyanin (KLH, Sigma, St. Louis, USA) conjugate for the vaccine: 5-allyl-5-(1-carboxyisopropyl)barbituric acid is transformed into 5-allyl-5(1-p-nitrophenyloxycarbonylisopropyl)barbituric acid through reaction of 10 mg of the free base with p-nitrophenol (12 mg) in a N,-N-Dimethylformamide solution during 24 hours at 4° C. The coupling to KLH (19) mg is thereafter done in a solution containing equal volumes of glycerin and water and 10 mg dicyclohexylcarbodiimide. After 24 hours incubation at 4° C., the mixture is dialysed with extensive exchange of Buffer against PBS pH 7.6. The degree of substitution of the drug at the carrier substance is calculated as an increase in optical density of the conjugate a 202 nm as compared to a KLH control solution (molar extinction coefficient of barbiturate is 19 500).

Immunization: 5 female Balb/C mice are injected subcutaneously 8 times in intervals of 2 weeks with 40 microgram per mice and dose of the morphine-BSA conjugate. Another group of the mice receives the barbiturate-KLH conjugate under the same conditions and a control group of 10 female Balb/C mice of the same age is treated with the buffer of the vaccine preparation without the vaccine.

Bleeding: The blood is taken from the tail vein.

Assay of the drug concentration: The High pressure Liquid Chromatography (HPLC) method of Joel et al. (1988, Chromatography, 430: 394–9 is used as a reference method in order to measure Morphine, morphine-6-glucuronide and morphine 3-glucuronide. The morphine as well as the barbiturate are likewise measured with a commercial enzyme immunoassay (EMIT, Shyva Corp., Palo Alto, USA) in accordance with the manufacturers instructions (EMIT operator's manual, Shyva Corporation, Palo Alto, USA). It is important for the evaluation of the vaccine to differentiate free drug from antibody bound drug. The EMIT assay is therefore modified as follows: the already diluted serum is purified from antibodies before the EMIT assay is executed. The sample is incubated at room temperature for two hours in a PBS Buffer, pH, 7.6 which contains CnBr-activated Sepharose 4 B, to which polyclonal rabbit antibodies against mice light chain immunoglobulins are linked (Pharmacia LKB Biotechnology, Bromma, Sweden).

Five mice, which have been vaccinated and 5 mice of the control group are 2 weeks after the last immunization injected with 0.5 mg per mouse. The serum samples are taken immediately after injection and 2 hours after injection and the quantity of the drug in the serum is determined with the help of the modified EMIT assay. It is still possible to detect the drug in the samples which were taken immediately after the injection of the drug, but 2 hours after injection the drug is no more detectable. The discrimination in the test system between positive and negative sample is determined to be 5 ng/ml as well for the barbiturates as for morphine. The interpretation of the test results is, that the antibodies have bound to the drug after a successful vaccination and the free drug is therefore no more detectable.

EXAMPLE 2

This experiment demonstrates, that the "immunity" against the drug is still present even after month. Two of the immunized mice of example 1 and three mice of the control group are injected 2 and 4 month after the first experiment with 0.5 mg morphine. One blood sample is taken as in the first experiment immediately after injection and 2 hours after injection and the serum is tested for morphine in the EMIT assay. The serum of the mice, which were prior immunized with the morphine -BSA conjugate is again negative and only the samples, which were taken immediately after injection show a positive result. The group of controls show in all samples detectable levels of morphine. The conclusion is made, that the vaccine is efficient over an extended time span.

EXAMPLE 3

This example serves to demonstrate the protective effect of specific antibodies, respectively specific immune serum containing the antibodies.

Two mice each of the control group receive 0.5 mg morphine (mice A and B) and 0.5 mg phenobarbital (mice C and D). Mice A and C receive each 0.5 ml of the serum of the mice which were previously vaccinated with the anti-morphine vaccine. Two hours after injection of the immune serum the blood samples are taken and examined for the presence of drug (modified EMIT assay). The mouse which has received morphine and anti-morphine serum shows no free morphine in the assay. The mouse which got morphine and anti-barbiturate serum, shows free morphine in the serum. An analogous phenomenon is seen with mice which have received phenobarbital: no free drug can be detected with the mouse which received the specific antibodies (mouse D). The mouse with the anti-morphine serum (mouse C) shows still traces of the drug in her serum.

This experiment can likewise be done with an anti-serum consisting of monoclonal antibodies or a mixture of monoclonl antibodies: an analogous result is expected.

What is claimed is:

1. A method for the manufacture of an immunogenic preparation for use as a vaccine,
   comprising the step of providing at least one substance linked as a hapten to a carrier substance in order to obtain a conjugate, wherein the hapten is a drug of abuse,
   processing the conjugate by purification and sterile filtration,
   preparing the purified and filtered conjugate in a number of doses in a physiologically acceptable solution,
   so that the cumulative dose of the conjugate per vaccination treatment is in excess of 0 micrograms and does not exceed a total amount of 320 micrograms absorbed by a body
   and induces the lasting protective effect of a vaccine no later than 4 months and over a time span of at least 8 months after the first application of said vaccine, despite repeated drug challenges.

2. A method for treating and/or preventing with a vaccine a physical or physical and psychological dependence of a subject on a drug of the kind provoking a psychotropic stimulating effect only when a sufficient quantity of said drug, or at least one component of said drug reaches a particular receptor in the human body, said subject having not necessarily been withdrawn from the drug,
   comprising the step of administering to said subject an amount of complex molecules capable of eliciting antibodies against said drug, or said component of said drug, in the human body,
   each of said complex molecules including a carrier substance and at least one molecule selected from said drug and said component of said drug, linked to said carrier as a hapten, wherein the amount of said complex molecules administered in the human body per application is in excess of 0 micrograms and does not exceed a total amount of 320 micrograms absorbed by the body
   and which induces the long lasting protective effect of a vaccine no later than 4 months and over an extended time span of at least 8 months after the first application, despite repeated drug challenges.

3. A method as claimed in claim 1, wherein said drug is a member selected from the group consisting of,
   opiates, marijuana, amphetamines, cocaine, barbituates, glutethimide, methyprylon, chloral hydrate, methaqualone, benzodiazepines, LSD, nicotine, anticholinergic drugs, antipsychotic drugs, tryptamine, other psychomimetic drugs, sedatives, phencyclidine, psilocybine, volatile nitrite, and other drugs inducing physical and/or psychological dependence.

4. A method as claimed in claim 2, wherein said drug is a member selected from the group consisting of, opiates, marijuana, amphetamines, cocaine, barbiturates, glutethimide, methyprylon, chloral hydrate, methaqualone, benzodiazepines, LSD, nicotine, anticholinergic drugs, antipsychotic drugs, tryptamine, other psychomimetic drugs, sedatives, phencyclidine, psilocybine, volatile nitrite, and other drugs inducing physical dependence and/or psychological dependence.

5. A method as claimed in claim 2, wherein said drug is nicotine.

6. A method as claimed in claim 1, wherein said carrier substance is Keyhole Lympet Hemocyanin.

7. A method as claimed in claim 2, wherein said carrier substance is Keyhole Lympet Hemocyanin.

8. A method for activating at least the B-cell branch of the immune system of a mammal against a drug which may cause a dependence in a vaccinated animal having specific antibodies against said drug as a result of a vaccination, so that an administration of said drug to said mammal elicits antibodies in said mammal's body, said method comprising the steps of linking a compound selected from said drug and a component of said drug, as a hapten, to a carrier substance having immunogenic properties, thereby synthesizing a hapten carrier conjugate, purifying said hapten carrier conjugate, providing the purified conjugate in a physiologically acceptable solution in doses containing an effective amount for vaccination by said purified conjugate, and administering said effective amount as the vaccine to said mammal.

9. A method as claimed in claim 8, wherein said drug is a member selected from the group consisting of, opiates, marijuana, amphetamines, cocaine, barbiturates, glutethimide, methyprylon, chloral hydrate, methaqualone, benzodiazepines, LSD, nicotine, anticholinergic drugs, antipsychotic drugs, tryptamine, other psychomimetic drugs, sedatives, phencyclidine, psilocybine, volatile nitrite, and other drugs inducing physical dependence and/or psychological dependence.

10. A method as claimed in claim 8, wherein said drug is nicotine.

11. A method as claimed in claim 8, wherein a dose of said purified conjugate comprises 40 µg of conjugate.

12. A method as claimed in claim 8, herein said carrier substance is Keyhole Lympet Hemocyanin.

13. A method for treating a physical and/or psychological dependence of a mammal on nicotine containing cigarettes, said method comprising the step of administering to said mammal an effective amount of complex molecules capable of eliciting antibodies against nicotine in the mammal's body, each of said complex molecules including at least one molecule of nicotine, linked to a carrier substance as a hapten capable of inducing antibodies against nicotine for treating said physical or physical and psychological dependence.

14. A method as claimed in claim 13 wherein said administering step comprises administration of an amount of said complex molecule which is ineffective to induce immunological tolerance.

15. A method as claimed in claim 14 wherein said carrier substance comprises a protein.

16. A method for preventing a physical and/or psychological dependence of a mammal on nicotine containing drugs, which can be smoked, said method comprising the step of administering to said mammal an effective amount of complex molecules capable of eliciting antibodies against nicotine in the mammal's body, each of said complex molecules including a carrier substance having immunogenic properties and at least one molecule of nicotine, linked to said carrier as a hapten in order to prevent a physical and/or psychological dependence of a mammal on nicotine containing smoke.

17. A method as claimed in claim 16 wherein said administering step comprises administration of an amount of said complex molecule which is ineffective to induce immunological tolerance.

18. A method as claimed in claim 17 wherein said carrier substance comprises a protein.

19. The method of claim 2, wherein said long lasting protective effect against said drug is instantly obtained by administering antibodies against said drug at the time of vaccination.

20. A method for the manufacturing of antibodies against drugs, which may induce dependence, comprising the steps of eliciting antibodies according to the method of claim 1 preparing said antibodies for use in a passive immunization against drugs, which may induce dependence.

\* \* \* \* \*

UNITED STATES PATENT AND TRADEMARK OFFICE
CERTIFICATE OF CORRECTION

PATENT NO. : 6,699,474 B1
DATED : March 2, 2004
INVENTOR(S) : Erich Hugo Cerny

It is certified that error appears in the above-identified patent and that said Letters Patent is hereby corrected as shown below:

Column 1,
Line 20, please insert the following: -- These antibodies can be used for the disintoxication of drug addicts, which have taken an overdose. --

Column 3,
Line 56, please delete "metaboliponent" and insert in lieu thereof -- metabolite --.

Signed and Sealed this

Sixth Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,699,474 B1
DATED : March 2, 2004
INVENTOR(S) : Erich Hugo Cerny

It is certified that error appears in the above-identified patent and that said Letters Patent is hereby corrected as shown below:

<u>Column 3,</u>
Line 57, after the word "drug" please insert the following phrase -- or a component of a drug --.

Signed and Sealed this

Twenty-fifth Day of October, 2005

JON W. DUDAS
*Director of the United States Patent and Trademark Office*